US010869753B1

(12) United States Patent
Otts et al.

(10) Patent No.: US 10,869,753 B1
(45) Date of Patent: Dec. 22, 2020

(54) ELECTROWETTING LENS COMPRISING PHASE CHANGE FLUIDS (71) Applicant: Verily Life Sciences LLC, Mountain View, CA (US)

(72) Inventors: Daniel Otts, Pleasanton, CA (US); Stein Kuiper, South San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 118 days.

(21) Appl. No.: 15/945,904

(22) Filed: Apr. 5, 2018

Related U.S. Application Data

(60) Provisional application No. 62/501,828, filed on May 5, 2017.

(51) Int. Cl.
*A61F 2/16* (2006.01)
*A61L 27/50* (2006.01)
(Continued)

(52) U.S. Cl.
CPC .......... *A61F 2/1627* (2013.01); *A61F 2/1635* (2013.01); *A61L 27/16* (2013.01);
(Continued)

(58) Field of Classification Search
CPC ................. A61F 2/1627; A61F 2/1635; A61F 2002/482; A61F 2250/0003; A61L 27/16; A61L 27/18; A61L 27/26; A61L 27/50
See application file for complete search history.

(56) References Cited

U.S. PATENT DOCUMENTS 8,382,280 B2    2/2013   Gupta et al.
8,390,939 B2    3/2013   Henriksen et al.
(Continued)

FOREIGN PATENT DOCUMENTS

WO     WO2007107589     *   9/2007

OTHER PUBLICATIONS

Mugele et al., "Electrowetting: from basics to applications", Topical Review, Journal of Physics: Condensed Matter, Published Jul. 1, 2005.
(Continued)

*Primary Examiner* — David H Willse
*Assistant Examiner* — Tiffany P Shipmon
(74) *Attorney, Agent, or Firm* — McDonnell Boehnen Hulbert & Berghoff LLP (57) ABSTRACT

An eye-implantable device including an electrowetting lens is provided that can be operated to control an overall optical power of an eye in which the device is implanted. A lens chamber of the electrowetting lens contains first and second fluids that are immiscible with each other and that differ with respect to refractive index. By applying a voltage to electrodes of the lens, the optical power of the lens can be controlled by affecting the geometry of the interface between the fluids. One or both of the fluids can have a melting point slightly below body temperature. Freezing such an oil or other fluid of the lens can prevent fouling of internal surfaces of the lens due to folding or other manipulation of the lens during implantation. Once implanted, the fluids are melted by body heat such that the optical power of the lens may be controlled.

12 Claims, 6 Drawing Sheets (51) Int. Cl.
*A61L 27/16* (2006.01)
*A61L 27/26* (2006.01)
*A61L 27/18* (2006.01)
*A61F 2/48* (2006.01)

(52) U.S. Cl.
CPC .............. *A61L 27/18* (2013.01); *A61L 27/26* (2013.01); *A61L 27/50* (2013.01); *A61F 2002/482* (2013.01); *A61F 2250/0003* (2013.01); *A61F 2250/0043* (2013.01); *A61F 2250/0056* (2013.01)

(56) References Cited

U.S. PATENT DOCUMENTS

| | | | |
|---|---|---|---|
| 8,460,376 | B2 | 6/2013 | Donitzky et al. |
| 8,665,526 | B2 | 3/2014 | Pugh et al. |
| 2007/0153405 | A1* | 7/2007 | Kuiper .................. G02B 3/14 |
| | | | 359/846 |
| 2008/0137213 | A1 | 6/2008 | Kuiper et al. |
| 2013/0229618 | A1 | 9/2013 | Otts et al. |
| 2013/0258277 | A1 | 10/2013 | Pugh et al. |
| 2014/0253870 | A1 | 9/2014 | Jiang et al. |
| 2015/0043085 | A1 | 2/2015 | Tsuji |
| 2016/0058553 | A1* | 3/2016 | Salahieh ............... A61F 2/1629 |
| | | | 623/6.13 |

OTHER PUBLICATIONS

B. Berge, "Liquid Lens Technology: Principle of Electrowetting Based Lenses and Applications to Imaging". IEEE. 2005, pp. 227-230.

Lu et al., "Tunable dielectric liquid lens on flexible substrate", Applied Physics Letters 103, 2013.

Mallin, "Flexible Membrane Liquid Lens", Optics & Optoelectronics, 2011 NNIN REU Research Accomplishments.

Li et al., "Fabrication and Characterization of Flexible Electrowettingon Dielectrics (EWOD) Microlens", NIH Author Manuscript, 2014, 432-441.

Li et al., "Electrowetting-driven variable-foxus microlens on flexible surfaces", Applied Physics Letters 100, 2012.

Bae et al., "Unique Fluid Ensemble including Silicone Oil for the Application of Optical Liquid Lens", Bull. Korean Chem. Soc. 2008, vol. 29, No. 4, pp. 731-735.

* cited by examiner

ELECTROWETTING LENS COMPRISING PHASE CHANGE FLUIDS

CROSS-REFERENCE TO RELATED APPLICATION

This application claims priority to U.S. Provisional Patent Application No. 62/501,828, filed May 5, 2017, which is incorporated herein by reference.

BACKGROUND

Unless otherwise indicated herein, the materials described in this section are not prior art to the claims in this application and are not admitted to be prior art by inclusion in this section.

Devices can be provided on the surface of the eye and/or within the eye to provide a variety of functions. In some examples, these functions can include functions to improve the ability of a person to view their environment (e.g., to provide an optical correction, to stimulate the retina directly) and/or to present additional visual information to the person (e.g., to present a heads up display or other indications to the person). Additionally or alternatively, these functions can include detecting a property of the body of a person (e.g., a blood glucose level, a concentration of an ion in the blood, a desired optical power of the eye) via the eye, e.g., by detecting forces, concentrations of analytes, electrical fields, or other properties related to the property of interest. Such functions can be provided by an intraocular device implanted within the eye (e.g., a retinal implant configured to stimulate the retina to restore vision, a device implanted within the lens capsule to provide a static and/or controllable optical power to the eye).

Such an eye-implantable device could include an electronically adjustable lens to provide a controllable amount of optical power to the eye. Such an electronically adjustable lens could be provided to correct for presbyopia. Presbyopia is a reduction in the eye's ability to naturally adjust its focal length, e.g., by deforming the crystalline lens of the eye. An electronically actuated lens could include a lens chamber that contains two or more immiscible fluids whose geometry within the lens chamber can be electronically controlled in order to control an overall optical power of the lens.

SUMMARY

Some embodiments of the present disclosure provide an eye-implantable device that includes an electrowetting lens. The electrowetting lens includes: (i) a lens chamber; (ii) a first substance that is disposed in the lens chamber and that has a first melting point that is less than 37 degrees Celsius; (iii) a second substance that is disposed in the lens chamber and that has a second melting point that is between 0 degrees Celsius and 37 degrees Celsius (iv) a first electrode that is disposed on an internal surface of the lens chamber in contact with the first substance; and (v) a second electrode that is disposed on an internal surface of the lens chamber in contact with at least one of the first substance or the second substance and that includes a dielectric coating. The second substance is immiscible with the first substance when the first substance and the second substance are both fluid. A refractive index of the second substance differs from a refractive index of the first substance when the first substance and the second substance are both fluid.

Some embodiments of the present disclosure provide a method that includes: (i) maintaining an eye-implantable device below a specified temperature; (ii) forming an incision through a cornea of an eye; (iii) inserting the eye-implantable device into the eye through the incision; and (iv) placing the eye-implantable device at a specified location within the eye. The eye-implantable device includes an electrowetting lens. The electrowetting lens includes: (i) a lens chamber; (ii) a first substance that is disposed in the lens chamber and that has a first melting point that is less than 37 degrees Celsius; (iii) a second substance that is disposed in the lens chamber and that has a second melting point that is between 0 degrees Celsius and 37 degrees Celsius; (iv) a first electrode that is disposed on an internal surface of the lens chamber in contact with the first substance; and (v) a second electrode that is disposed on an internal surface of the lens chamber in contact with at least one of the first substance or the second substance and that includes a dielectric coating. The specified temperature is less than or equal to at least one of the first melting point or the second melting point. The second substance is immiscible with the first substance when the first substance and the second substance are both fluid. A refractive index of the second substance differs from a refractive index of the first substance when the first substance and the second substance are both fluid.

These as well as other aspects, advantages, and alternatives, will become apparent to those of ordinary skill in the art by reading the following detailed description, with reference where appropriate to the accompanying drawings.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Implantable devices could be located within an eye of a person to provide a static or adjustable optical power to the eye. Such a static or adjustable optical power could be provided to correct a lack or loss of optical power and/or accommodation in the eye, e.g., to correct for presbyopia, myopia, hyperopia, astigmatism, injury or damage to the eye, removal of the crystalline lens of the eye, or to correct for some other condition of the eye. Such implantable devices could be located within the lens capsule, within the anterior chamber, within the fibrous wall of the eye, proximate to the retina, or in some other location(s) of the eye according to an application. Such an eye-implantable device could include an electronically adjustable lens to provide a controllable amount of optical power to the eye. An electronically adjustable lens could include an electrowetting lens that includes two or more immiscible fluids whose geometry within the electrowetting lens can be electronically controlled (e.g., by applying an electrical voltage to two or more electrodes of the lens) in order to control an overall optical power of the electrowetting lens. Such an adjustable lens could be configured in some other way to control an overall optical power of the lens, e.g., by pumping an amount of one or more immiscible fluids into or out of a lens chamber (e.g., via electrowetting or some other process).

To facilitate implantation of such an eye-implantable device, it can be beneficial for the device to be flexible. Such a flexible device could be bent, folded, or otherwise manipulated to permit implantation. The device could subsequently be unfolded or otherwise manipulated into a flat or otherwise operational state. For example, the eye-implantable device could be rolled up or folded (e.g., in half, in thirds) to facilitate insertion into the eye by way of an incision that is smaller than the unfolded size of the device (e.g., via an incision that is smaller than an unfolded diameter of a lens of the eye-implantable device). Such flexibility could improve biocompatibility, speed or otherwise improve the process of implantation, permit detection of forces applied to the device, or could provide some other benefit.

However, where such a device includes an electrowetting or otherwise configured lens that contains two or more immiscible fluids, folding or otherwise manipulating the lens can cause the immiscible fluids within the lens to disperse into each other (e.g., the fluids could form an emulsion, a suspension, or some other mixture wherein droplets of one of the fluids are dispersed into the other fluid and/or vice versa), to contact and wet surfaces that they should not come into contact with, or to result in other deleterious effects. For example, when an oil (or other nonpolar fluid) of a lens comes into contact with an interior surface of the lens that is intended to be in contact with saline (or with some other polar fluid) of the lens, the oil can wet and/or foul the interior surface. This wetting and/or fouling can result in decreased clarity or some other deleterious effect on the optical properties and/or functioning of the lens.

To reduce such deleterious effects, one or both of the fluids of such a lens could be made solid for the purposes of implantation and later made fluid (e.g., once implanted into an eye) to permit electronic control of the optical power of the lens. This could include freezing or otherwise solidifying one or both of the fluids before implantation. The melting point of such substances could be below body temperature such that exposure to the environment within the eye results in melting of the substances, returning them to an operational fluid state. The melting point of such a substance could be above room temperature to facilitate storage and/or freezing of the fluid simply by exposing it (e.g., storing it inside) an environment at room temperature. Additionally or alternatively, an eye-implantable device containing one or more such a substance could be cooled prior to and/or during implantation so that the substance remains frozen, reversibly congealed, reversibly cross-linked, vitrified, or otherwise solid until the device has been positioned within an eye.

Such eye-implantable devices could include electronics, antennas, voltage regulators, batteries, photovoltaic cells, sensors, or other elements to facilitate operations of the device, e.g., to provide a controllable optical power to an eye. Such eye-implantable devices could receive, from outside of the eye, radio frequency, optical, infrared, acoustic, or other forms of power to power the operations of the device, e.g., from a contact lens, eyeglasses, a head-mountable device, or some other source. The eye-implantable device could receive wireless transmissions to specify an amount of optical power to provide, via controlling the optical power of the lens, to the eye, could operate a sensor to detect a physical variable (e.g., an accommodation force exerted by ciliary muscles of the eye) to specify the amount of optical power to provide, or the eye-implantable device could use some additional or alternative source of information or commands to determine an amount of optical power to provide to an eye.

II. Example Eye-Implantable Device

An eye-implantable device (e.g., an intraocular lens, or IOL) can include electronics and an electronically adjustable lens that are operable to provide a controllable optical power (e.g., a controllable diopter, focal length, or other form of optical power or refractive property) to an eye in which the device is implanted. Such an eye-implantable device could include haptics or other formed features, or be formed according to a particular shape, such that the eye-implantable device can be implanted in or at a particular location within an eye, e.g., within the lens capsule of the eye following removal of the crystalline lens, within the anterior chamber of the eye, within the posterior chamber of the eye, along an optical axis of the eye. A controller, battery, antenna, sensors, or other elements can be provided to power the device, to determine a specified amount of optical power to provide to the eye (e.g., based on a sensor output, based on a received wireless command), and to operate the electronically adjustable lens to provide such a specified optical power by applying a voltage, current, or other electrical signal to the electronically adjustable lens. In some examples, the electronically adjustable lens could be an electrowetting lens.

Note that, while reference is made throughout this application to electrowetting lenses of eye-implantable devices, the embodiments provided herein could be applied to other applications. For example, phase-changing fluid(s) could be provided as part of a flexible lens of an eye-implantable device that is configured to control an optical power of the lens via some process other than or in addition to electrowetting. Such a device could be configured to pump one or more immiscible fluids into or out of a lens chamber of a lens using a piezo actuator, a electrowetting actuator, a shape-memory actuator, or other actuator to pump the one or more fluids into or out of the lens chamber.

Figure 1A:
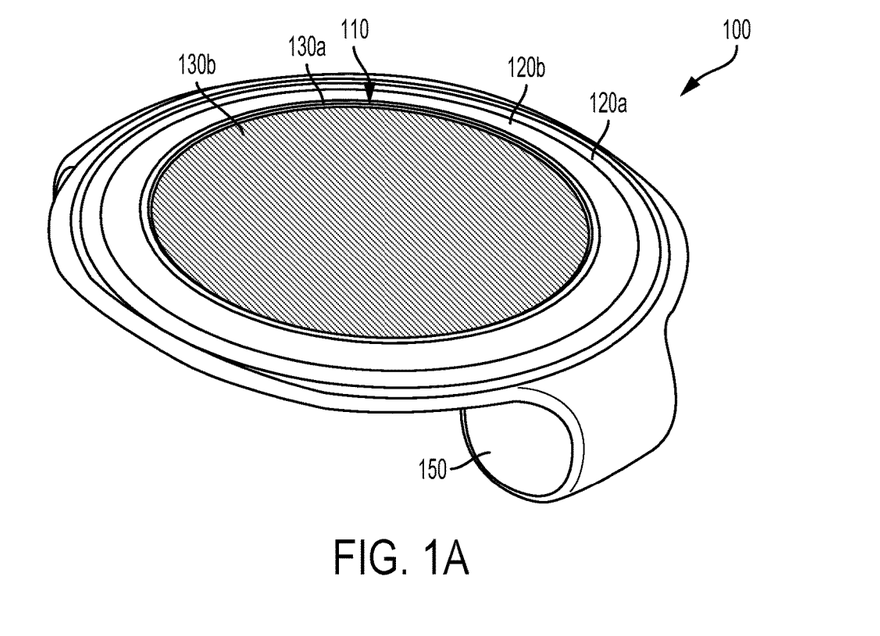
FIG. 1A is a perspective view of an example eye-implantable device.
Figure 1B:
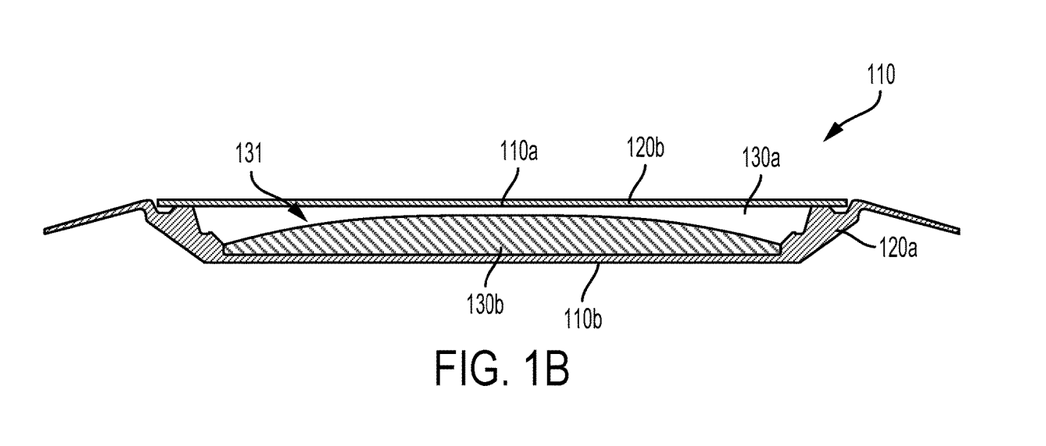
FIG. 1B is a side cross-section view of an electrowetting lens of the example eye-implantable device shown in FIG. 1A.

FIG. 1A is a bottom view of an example eye-implantable device 100. FIG. 1B is a cross-sectional view of an electrowetting lens 110 of the example eye-implantable device 100 shown in FIG. 1A. It is noted that relative dimensions in FIGS. 1A and 1B are not necessarily to scale, but have been rendered for purposes of explanation only in describing the arrangement of the example eye-implantable device 100 and electrowetting lens 110 thereof. The eye-implantable device 100 includes electronics 150 configured to operate the electrowetting lens 110 to provide a controllable optical power and to provide other operations of the eye-implantable device 100. The electronics 150 may include controllers, voltage regulators, antennas, photovoltaic cells, sensors, electrodes, transmitters, receivers, batteries, or other components. The electronics 150 may be configured to receive and/or store wireless energy to power the device 100 (e.g., visible light energy, infrared light energy, radio frequency electromagnetic energy, acoustic energy), to communicate with external devices or systems (e.g., to receive program updates, to receive a commanded optical power level), to detect one or more physical variables (e.g., a light level, a pupil diameter, an intraocular pressure, a voltage related to activity of muscles of the eye, a force exerted by ciliary muscles of the eye, a concentration of one or more substances in the eye) that may be used to determine an optical power to provide or that may be used in some other way, to operate the electrowetting lens 110, or to facilitate some other applications of the device 100.

The electrowetting lens 110 and/or other elements of the eye-implantable device 100 may be formed of one or more polymeric materials. The polymeric materials can include substantially transparent materials to allow incident light to be transmitted to the retina of the eye through the electrowetting lens 110 of the eye-implantable device 100. The polymeric materials can include biocompatible materials similar to those employed to form implants, vision correction lenses, IOLs, or other implantable devices, such as polyethylene terephthalate ("PET"), polymethyl methacrylate ("PMMA"), silicone hydrogels, rigid, gas-permeable polymeric materials, barrier materials that block diffusion of gases or other substances, combinations of these, etc. The polymeric materials could include flexible and/or foldable water-permeable materials. For example, the polymeric material could include a copolymer comprising 2-phenylethyl acrylate units and 2-phenylethyl methacrylate units. Units of a polymer or copolymer could be cross-linked by an applicable cross-linking agent or unit, e.g., by 1,4-butanediol diacrylate units, 1,6-hexanediol diacrylate units, or some other crosslinking agent or combination of such agents. Such flexible and/or foldable materials may be included in the construction of the device 100 to permit the device 100 to be rolled, folded, or otherwise manipulated such that the device 100 may be inserted through an incision that is smaller than, e.g., the diameter of the unrolled or un-folded electrowetting lens 110. The eye-implantable device 100 may include coating materials disposed on one or more external or internal surfaces of the device, e.g., to improve a biocompatibility of the device, to control a surface energy of an internal surface of the electrowetting lens (e.g., to encourage or prevent wetting of a surface that at least partially encloses a lens chamber by one or more fluids within the lens chamber), to prevent to passage of ions or other substances, or to provide some other benefit.

The electrowetting lens 110 includes a lens chamber 131 in which are disposed a first fluid 130a and a second fluid 130b. The lens chamber 131 is formed from first 120a and second 120b elements formed, respectively, as a cup and a flat lid. At least a portion of the first 120a and/or second 120b elements of the electrowetting lens 110 could be formed from a polymeric material (e.g., one of the polymeric materials listed elsewhere herein) that is permeable to water in aqueous humor of an eye (e.g., from a copolymer comprising 2-phenylethyl acrylate units and 2-phenylethyl methacrylate units cross-linked by 1,4-butanediol diacrylate units). Such a water-permeable polymeric material, or other polymeric or non-polymeric materials of the electrowetting lens 110, could be flexible such that the electrowetting lens 110 can be rolled, folded, or otherwise manipulated, e.g., to facilitate insertion through an incision in an eye. Additionally or alternatively, one or more sealant materials (e.g., a sealant material used to adhere the first element 120a to the second element 120b) of the electrowetting lens 110 could be permeable to water in aqueous humor of an eye.

Note that the illustrated first 120a and second 120b elements of the chamber 131 of the electrowetting lens 110 are intended as non-limiting example embodiments. For example, an electrowetting lens and/or a lens chamber thereof as described herein could be constructed and/or formed from more or fewer elements (e.g., from a front element, a rear element, and an annular element) than the two shown and/or could be constructed from elements configured differently from the elements 120a, 120b illustrated here. Different elements of an electrowetting lens could be composed of the same material (e.g., the elements 120a, 120b of the electrowetting lens 110 could both be composed of a copolymer comprising 2-phenylethyl acrylate units and 2-phenylethyl methacrylate units). Alternatively, elements of an electrowetting lens could be composed of different materials (e.g., the first element 120a could be composed of a copolymer comprising 2-phenylethyl acrylate units and 2-phenylethyl methacrylate units and the second element 120b could be composed of polyethylene terephthalate).

The first 130a and second 130b fluid are immiscible (e.g., the first fluid 130a could be saline or some other aqueous fluid and the second fluid 130b could be an oil or some other nonpolar fluid) and differ with respect to refractive index. Thus, a surface of contact between the first 130a and second 130b fluids (e.g., a convex shape, as shown in FIG. 1B) could provide an optical power (e.g., a diopter, a nonzero focal length) related to the difference in the refractive indices of the fluids 130a, 130b and the shape of the surface of contact.

The electrowetting lens 110 further includes at least two electrodes (not shown) disposed on respective internal surfaces of elements that form the lens chamber 131. Voltages, currents, or other electrical signals can be applied to the at least two electrodes to electronically control the shape of the first 130a and second 130b fluids (e.g., to control a shape of a contact surface between the two fluids 130a, 130b) in order to control an optical power of the electrowetting lens 110. In order to allow the electrowetting lens 110 to be flexed, folded, rolled, or otherwise manipulated during implantation while retaining the functionality of the lens, the electrodes could be composed of gold, aluminum, silver nanowires, or some other material or coating that can be flexed and maintain an overall level of electrical conductivity across the area of the electrodes. Such materials could be applied mechanically (e.g., as a foil) or via some other process (e.g., via sputtering, CVD, PVD, application as a solution followed by evaporation of a solvent of the solution).

One of the first 130a or second 130b fluid may include an aqueous solution. Such an aqueous solution may be electrically conductive, e.g., to facilitate transmission of electrical voltages or currents through the aqueous solution in order to control the shape of the interface between the aqueous solution and another fluid of the electrowetting lens 110. In some examples, the aqueous solution may be substantially isotonic relative to the aqueous humor of an eye into which the eye-implantable device 100 is implanted. The aqueous solution could have an osmolality corresponding to the osmolality of the aqueous humor such that, if the lens chamber is permeable to water in the aqueous humor, a small or substantially zero amount of net water flow occurs between the aqueous solution within the lens chamber and the aqueous humor of the eye. This could include the aqueous solution having an osmolality between 298 milliosmoles per kilogram and 310 milliosmoles per kilogram, or an osmolality between 300 milliosmoles per kilogram and 308 milliosmoles per kilogram, or an osmolality between 302 milliosmoles per kilogram and 306 milliosmoles per kilogram, or an osmolality between 303 milliosmoles per kilogram and 305 milliosmoles per kilogram.

The overall optical power provided by the eye-implantable device 100 and/or the electrowetting lens 110 (e.g., to an eye in which the device 100 is implanted) could be related to the geometry, refractive index, or other properties of elements of the eye-implantable device 100. As noted above, this could include the shape of a contact surface between the first 130a and second 130b fluids within the lens chamber 131 and the refractive indices of the fluids 130a, 130b.

Other elements of the eye-implantable device 100 could provide a static and/or controllable optical power. For example, the front and/or rear surfaces of the electrowetting lens 110 could have curved surfaces to provide an optical power related to a change in refractive index between materials on either side of those surfaces (e.g., between a polymeric material of the first 120a and/or second 120b elements and aqueous humor of an eye, or between the polymeric material and one of the first 130a or second 130b fluids).

Components of the eye-implantable device 100 and/or electrowetting lens 110 (e.g., the first 120a or second 120b elements forming the lens chamber 131) can be formed to have a curved shape in a variety of ways. For example, techniques similar to those employed to form vision-correction contact lenses and/or intraocular lenses, such as heat molding, injection molding, spin casting, etc. can be employed to form polymeric materials into components of the eye-implantable device 100. Further, an eye-implantable device as described herein could have a different shape from that of the illustrated eye-implantable device 100. For example, an eye-implantable device could include haptics or other formed elements to maintain the eye-implantable device at a particular location within an eye (e.g., within a lens capsule of an eye), to detect accommodation forces exerted by ciliary muscles of an eye, or to provide some other benefit.

Figure 1C:
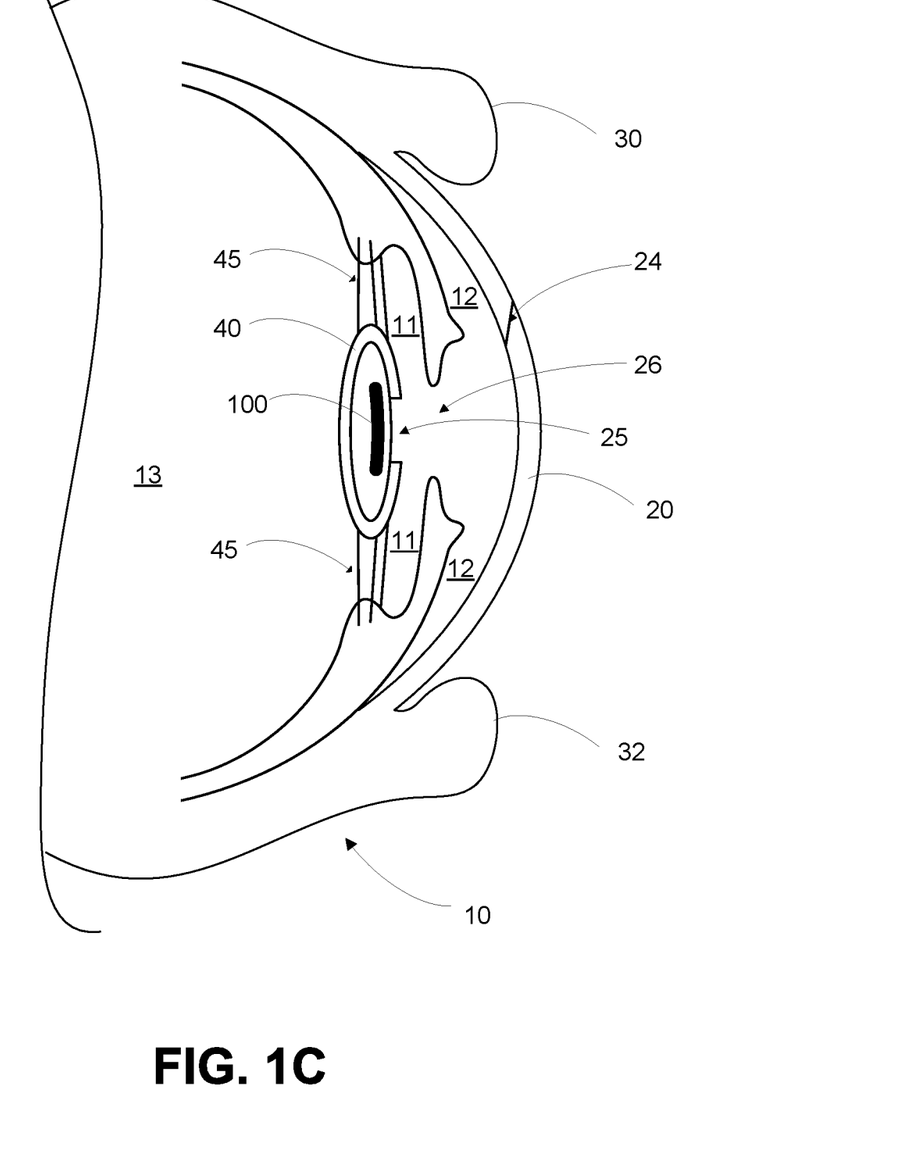
FIG. 1C is a side cross-section view of the example eye-implantable device shown in FIGS. 1A and 1B located within an eye.

FIG. 1C is a side cross-section view of the example eye-implantable device 100 while implanted within an eye 10. The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception.

The light received by the retina is transmitted, in the unaltered eye, through the crystalline lens, being refracted by the lens such that light received from the environment arrives in focus at the retina. The crystalline lens is located within the lens capsule 40 of the eye, which is connected, via the zonules 45, to accommodation muscles (e.g., ciliary muscles) and other elements of the eye. Accommodation forces transmitted through the zonules (e.g., forces generated by the accommodation muscles, forces generated by intrinsic elasticity of the zonules, or forces generated by other sources) act, in the eye, to deform the crystalline lens within the lens capsule 40, controlling the optical power provided by the crystalline lens.

As shown in FIG. 1C, the crystalline lens of the eye 10 has been removed and the eye-implantable device 100 has been surgically emplaced within the lens capsule 40 such that light received by the retina is transmitted through the electrowetting lens 110 of the eye-implantable device 100, being refracted by the electrowetting lens 110 and/or other elements of the eye-implantable device 100. Thus, the eye-implantable device 100 can be operated such that light received from the environment may arrive in focus at the retina, e.g., by operating the electrowetting lens 110 to provide a specified optical power.

The eye-implantable device 100 has been inserted into the eye 10 through an incision 24 formed in the cornea 20 of the eye 10 and then positioned within the lens capsule 40. In order to position the device 100 within the lens capsule 40, a hole 25 has been formed in the lens capsule 40 (e.g., via continuous curvilinear capsulorhexis) and the crystalline lens has been removed (e.g., via ultrasonic phacoemulsification). An eye-implantable device as described herein may be positioned in alternative locations within the eye 10, e.g., within the posterior chamber 11, anterior chamber 12, or in the vitreous humor 13 of the eye 10.

It is noted that relative dimensions in FIG. 1C are not necessarily to scale, but have been rendered for purposes of explanation only in describing the arrangement of the example eye-implantable device 100 within the eye 10. Further, such an implanted device could include multiple elements, located, e.g., in multiple different locations. Such multiple elements could be connected via a cable or by some other means. For example, such an implanted device could include a power reception element and controller that is disposed in the posterior capsule 11 and that is operable to receive wireless power from an eye-mountable device or other external system (not shown) and an electrowetting lens that is disposed within the lens capsule 40 could be operated, by the controller, via a tether connecting the controller and the electrowetting lens, using power from the power reception element.

The eye-implantable device 100 may be rollable, foldable, or otherwise flexible to permit its being rolled, folded, or otherwise manipulated into a smaller shape. This could permit the device 100 to be inserted through a smaller incision through the cornea 20. For example, the device 100 could be rolled up, folded in half, folded in thirds, or manipulated in some other way to permit the device 100 to be inserted through an incision 24 that is less than four millimeters long. In some examples, the device 100 may be rollable, foldable, or otherwise manipulable such that it can be inserted through an incision 24 that is less than 2 millimeters long. In such examples, the eye-implantable device 100 may be unrolled, unfolded, or otherwise manipulated into an operation shape or state (e.g., a substantially flat state) after it is inserted through the incision 24 in the cornea 20 and/or after it has been inserted through some other formed hole or incision (e.g., the hole 25 in the lens capsule) or through some other opening or feature of the eye (e.g., the pupil 26 of the eye 10) to position the device 100 in a specified location of the eye 10.

Note that, while the electrowetting lens 110 is illustrated as containing two fluids 130a, 130b, an electrowetting lens as described herein could be manufactured and distributed containing only one fluid (e.g., an aqueous conductive solution). A second fluid (e.g., an oil or other nonpolar fluid) could later be added to the electrowetting lens. Such an electrowetting lens containing only a single fluid could be provided to simplify implantation or fabrication of the electrowetting lens. For example, by folding such an electrowetting lens, inserting it into position in an eye, and unfolding the lens before addition of the second fluid, fouling and/or wetting of internal surfaces of the electrowetting lens by the second fluid (e.g., due to the second fluid contacting the internal surfaces as a result of folding, bending, or otherwise manipulating the electrowetting lens during implantation) can be avoided. The second fluid can then be added after the electrowetting lens has been unfolded (e.g., via injection through a septum of the electrowetting lens using a needle, via a tubule connected to the electrowetting lens).

An electrowetting lens (e.g., 110) as described herein may be configured in a variety of ways such that a shape of two or more fluids (e.g., a polar fluid and a nonpolar fluid) can be controlled by the application of a voltage, current, or other electrical signal to electrodes of the electrowetting lens. In some examples, this could include applying, via the electrodes, an electrical field that changes the effective surface energy, surface tension, interfacial energy, or other surface properties of one or more surfaces that at least partially enclose and/or form a lens chamber of the electrowetting lens such that a first one of the immiscible fluids retreats or advances across the one or more surfaces. As the first fluid retreats or advances across the one or more surfaces, the overall shape of the first fluid, and of a contact surface between the first fluid and a second fluid that is immiscible with the first fluid, may change. If the first fluid and second fluid have differing refractive indices, light may be refracted when passing through the electrowetting lens and an amount of that refraction (and a corresponding optical power of the electrowetting lens) could be related to the shape of the contact surface. Thus, the overall optical power of the electrowetting lens can be electronically controlled by applying electrical signals to the electrodes of the electrowetting lens to, e.g., control the shape of one or more fluids within the electrowetting lens and/or to control a shape of a contact surface between such fluids of the electrowetting lens.

Figure 2A:
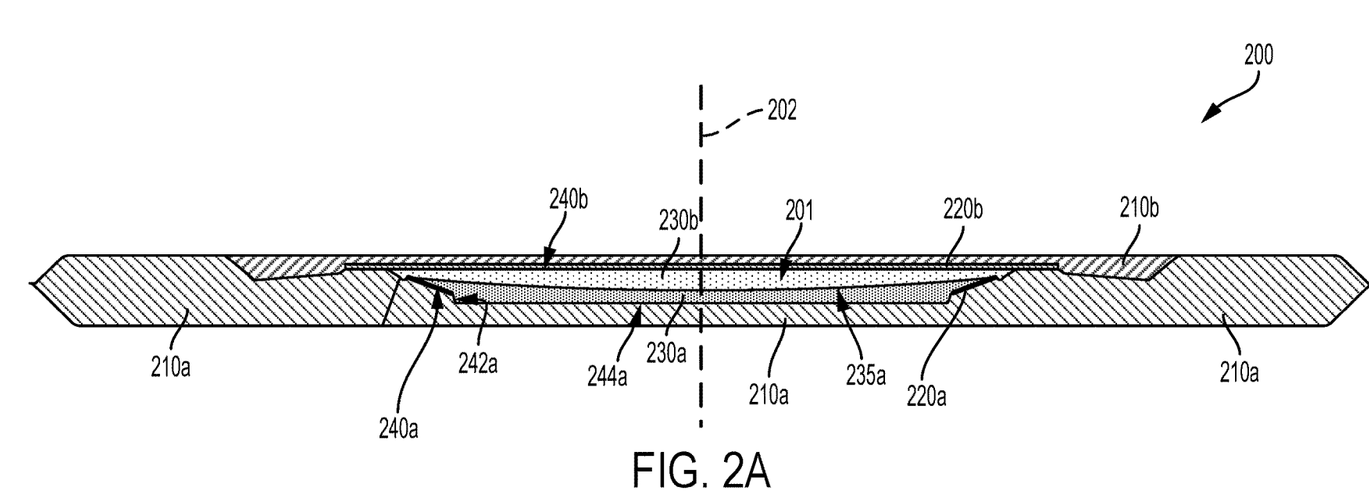
FIG. 2A is a side cross-section view of an example eye-implantable device.

FIG. 2A illustrates a cross-sectional view of an example electrowetting lens 200 during a first period of time. The electrowetting lens 200 includes a lens chamber 201 formed from first 210a and second 210b elements. In the example electrowetting lens 200, the lens chamber 201 is radially symmetric about a center line 202. A first electrode 220a is formed along a first internal surface 240a of the first element 210a and takes the form of an inclined ring. A second electrode 220b is formed along a second internal surface 240b of the second element 210b. A first fluid 230a is disposed within the lens chamber 201 and, during the first period of time illustrated in FIG. 2A, is in contact with the first internal surface 240a, the first electrode 220a, a third internal surface 242a, and a fourth internal surface 244a. A second fluid 230b is also disposed within the lens chamber 201 and is, during the first period of time, in contact with the second internal surface 240b and the second electrode 220b. During the first period of time, a contact surface between the first fluid 230a and the second fluid 230b has a first shape 235a. The first 230a and second 230b fluids are immiscible (e.g., the first fluid 230a is a nonpolar fluid and the second fluid 230b is a polar fluid) and have differing refractive indices.

As the first 230a and second 230b fluids differ with respect to refractive index, light that passes through the contact surface (e.g., light that is passing through the electrowetting lens 200 along the center line 202) may be refracted. A degree or amount of the refraction, and a related optical power of the electrowetting lens 200, may be related to the shape of the contact surface between the first fluid 230a and the second fluid 230b.

The refractive indices of the two fluids 230a, 230b may differ by a specified amount. The optical power of the electrowetting lens 200 (e.g., the controllable range of optical powers of the electrowetting lens 200) may be related to the magnitude of the difference between the refractive indices. The refractive indices of the two fluids 230a, 230b could differ by more than 0.1. The difference between the refractive indices could be controlled by controlling and/or modifying the refractive index of one or both of the fluids 230a, 230b.

The refractive index of an aqueous fluid (e.g., the second fluid 230b) may be approximately equal to 1.33, the refractive index of water. Alternatively, butanediol or some other substance(s) could be added to such an aqueous solution such that the refractive index of the aqueous solution differs from 1.33. In examples where a substance is added to an aqueous (or other) fluid of the electrowetting lens 200, the electrowetting lens 200 may include a seal or coating to seal the lens chamber (e.g., to hermetically seal the lens chamber) to prevent such a substance from exiting the electrowetting lens 200 and entering the aqueous humor of an eye.

Properties of a nonpolar fluid (e.g., the first fluid 230a) could additionally or alternatively be specified to control the refractive index of the nonpolar fluid. This could include adding substances to the nonpolar fluid. For example, a phenylated silicone oil (e.g., polyphenylmethylsiloxane) could be added to a silicone oil (e.g., to polydimethylsiloxane) to increase its refractive index. Additionally or alternatively, a ratio of components of a nonpolar fluid could be specified to control the refractive index of the nonpolar fluid. For example, a ratio between a first linear alkane (e.g., hexadecane) and a second linear alkane (e.g., nonadecane) could be specified to control the refractive index of the nonpolar fluid. Yet further, a polymer length, a polydispersity, a degree of branching, or some other properties of a nonpolar fluid could be specified to control the refractive index of the nonpolar fluid and/or to control some other property (e.g., melting point, viscosity, surface energy, density) of the nonpolar fluid.

The shape of the contact surface can be controlled by applying an electrical signal to the electrodes 220a, 220b, e.g., by applying an electrical voltage to the electrodes 240a, 240b. The voltage applied to the electrodes 220a, 220b may be related to the steady-state (e.g., following any transient changes in the electrowetting lens resulting from changes in the applied voltage) optical power of the electrowetting lens 200 and/or the shape of the contact surface between the fluids 230a, 230b. The specific relationship could be based on an effect on the surface energy of the first internal surface 240a relative to each of the fluids 230a, 230b, to an effective capacitance between the first electrode 220a and the second electrode 220a via a conductive second fluid 230b (e.g., via a second fluid 230 that includes a conductive, aqueous solution and that is in conductive and/or capacitive electrical contact with the second electrode 220b), or to some other factors.

The first electrode 220a and second electrode 220b could include conductive materials (e.g., aluminum, gold, copper, or other materials) disposed on respective internal surfaces of the first element 210a and second element 210b. Such deposition could include forming the electrodes in place (e.g., by sputtering, chemical vapor deposition, polymerization, deposition of a carrier fluid containing nanowires or other materials in suspension followed by evaporation of the carrier fluid, by photolithography or other processes for patterning or etching materials in place) and/or forming the electrodes and subsequently disposing them on internal surfaces of the elements 210a, 210b (e.g., by using an adhesive to adhere a metal foil, wire, rod, cone, textured surface, or other formed conductive material to a surface of one or both of the elements 210a, 210b). Additionally or alternatively, one or both of the electrodes 220a, 220b could include wires, rods, cones, textured surfaces, or other elements that are disposed on and/or that penetrate through an internal surface of one or both of the elements 210a, 210b and that protrude into the lens chamber 201.

One or both of the electrodes could further include a dielectric layer disposed between such a conductive material and the inside of the lens chamber 201. For example, the first electrode 220a could include such a dielectric layer. Such a dielectric layer could be provided to prevent large, direct currents from passing from the first electrode 220a into one or both of the first 230a or second 230b fluids, to provide a capacitive electrical coupling between the first electrode 220a and such fluids, to limit an amount of charge that can be transmitting into such fluids via the first electrode 220a, or to provide some other benefits.

Such a dielectric layer could be a separate material (e.g., parylene) deposited on the conductive material (e.g., via CVD, spin coating, or some other process). Additionally or alternatively, the dielectric layer of the first electrode 220a could be formed from the conductive material of the electrode, e.g., the dielectric layer could be a nonconductive layer of aluminum oxide formed by oxidation of an underlying aluminum metal of the first electrode 220a. Such a dielectric layer could be formed via anodization or other electrically-driven reactions at the surface of the electrode. Additionally or alternatively, such a dielectric layer could be formed by redox reactions between the fluids in the lens chamber 201 and the material of the electrode.

In some examples, the formation and/or maintenance of such a dielectric layer could be negatively impacted by the presence of certain ions within the lens chamber 201 (e.g., dissolved in one or both of the fluids 230a, 230b). For example, the presence of chloride ions could act to pit or otherwise damage a dielectric layer of aluminum oxide that has formed on the surface of an aluminum electrode. In such examples, a barrier could be formed from a chloride-impermeable material to prevent chloride ions present in the aqueous humor (or in some other environment to which the lens 200 is exposed) from entering the lens chamber 201 or from entering some other material or volume of the lens 200. Such a material could include a polymeric material, a metal foil or deposited metal layer, or some other material(s). Such materials could be substantially transparent to visible light.

Figure 2B:
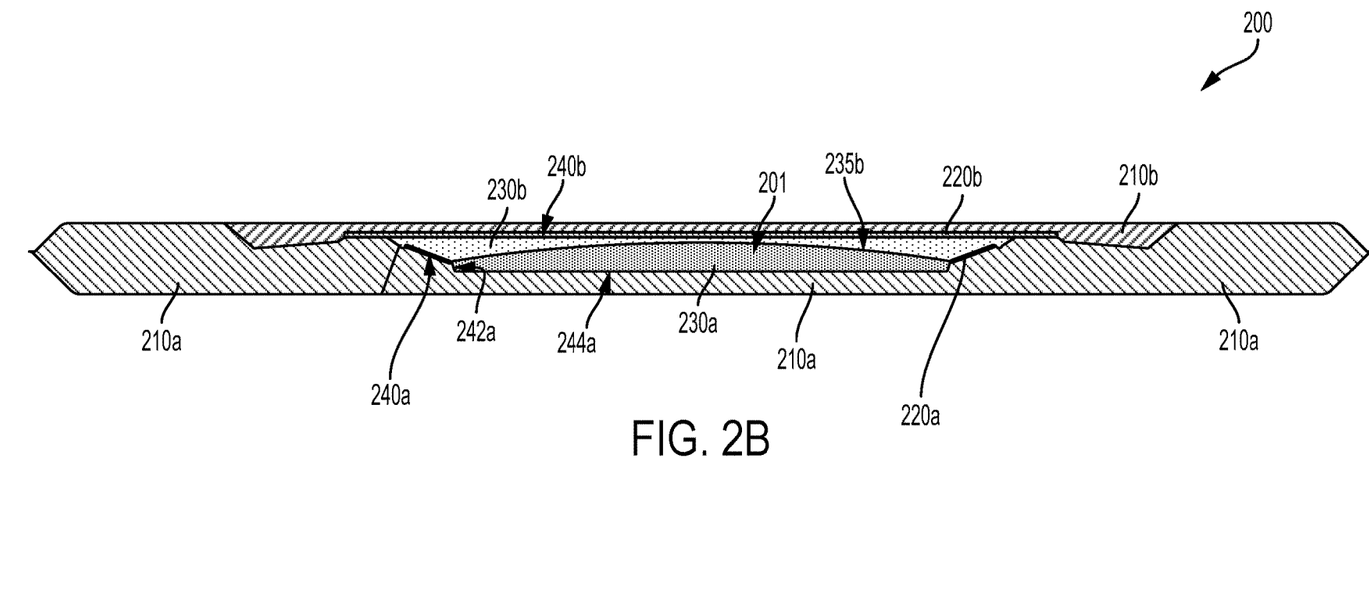
FIG. 2B is a side cross-section view of an example eye-implantable device shown in FIG. 2A.

The voltage between the electrodes 220a, 220b could be controlled in order to control the optical power of the electrowetting lens 200 by controlling the shape of the contact surface between the fluids 230a, 230b. FIG. 2B illustrates the electrowetting lens 200 during a second period of time during which a voltage is being applied to the electrodes 220a, 220b such that the contact surface between the first fluid 230a and the second fluid 230b has a second shape 235b. As a result, the optical power of the electrowetting lens 200 during the second period of time is different than the optical power of the electrowetting lens 200 during the first period of time.

The particular shape of the contact surface and/or of the geometry of the fluids 230a, 230b could be related to the applied voltage and to a variety of other factors. Such factors could include the interfacial energy between the fluids 230a, 230b, the interfacial energy between the fluids 230a, 230b and the internal surfaces 240a, 242a, 244a, 240b, the geometry of the internal surfaces 240a, 242a, 244a, 240b, a geometry of the electrodes 220a, 220b, and/or a geometry of a dielectric layer of the first electrode 220a. One or more of these factors could be specified in order to affect the shape of the contact surface between the fluids 230a, 230b, to affect the geometry and/or location of the fluids 230a, 230b within the lens chamber 201, to affect the relationship between an applied voltage and the optical power of the electrowetting lens 200, or to affect some other property of interest of the electrowetting lens 200.

This could include adding surfactants, polar and/or ionic substances, nonpolar substances, to the fluid(s) or otherwise specifying a composition of the first 230a and/or second 230b fluids to control an interfacial energy between the fluids 230a, 230b and/or to control an interfacial energy between the fluids and the internal surfaces 240a, 242a, 244a, 240b. Additionally or alternatively, the composition of the material composing the internal surfaces 240a, 242a, 244a, 240b could be specified to control the interfacial energy between the internal surfaces and the fluids.

This could include selecting the bulk materials of the first 210a and second 210b elements and/or providing one or more coatings or surface treatments to the internal surfaces of the first 210a and/or second 210b elements. For example, the first fluid 230a could be an oil or other nonpolar fluid and one or more of the first 240a, third 242a, or fourth 244a internal surfaces could be superhydrophobic or otherwise hydrophobic. Further, the second fluid 230b could be a polar fluid (e.g., could include a saline solution or other aqueous solution) and the second 240b internal surface could be superhydrophilic or otherwise hydrophilic (e.g., by including a surface coating, by including a surface features or textures, by having been exposed to an oxidization process, or by some other means).

The distribution of such coatings or materials on the internal surfaces of the first 210a and/or second 210b elements and/or the geometry of such surfaces could be specified to center the first fluid 230a along the center line 202 or along some other specified axis of the electrowetting lens 200. This could include applying different coating or other material to internal surfaces according to distance from the center line 202. Additionally or alternatively, a thickness or other property of a dielectric of the first electrode 220a could vary according to distance from the center line 202 such that, when a voltage is applied between the electrodes 220a, 220b, electrical and/or interfacial forces applied to the first 230a and/or second 230b fluids tend to center the first fluid 230a along the center line 202 and/or to conform a boundary between the fluids 230a, 230b on the first internal surface 240a to a circle centered on the center line 202.

The lens chamber 201 could be permeable to water or other substances (e.g., ions) in aqueous humor of an eye. This could include the first 210a and/or second 210b elements being composed at least partially of a polymeric material that is permeable to water (or other substances) in the aqueous humor. In examples wherein the lens chamber is permeable to a substance that is present in the aqueous humor, one or both of the fluids 230*a*, 230*b* could include a concentration of the substance corresponding to the concentration of the substance in the aqueous humor, e.g., to prevent a net flow of the substance from the aqueous humor into the fluids 230*a*, 230*b* or vice versa.

Additionally or alternatively, the lens chamber could be made impermeable to such substances in the aqueous humor and/or to substances in one or both of the fluids 230*a*, 230*b*. For example, one of the fluids could be a conductive fluid that includes butanediol, and the lens chamber could be made impermeable to butanediol and/or could be hermetically sealed. This could include constructing the lens chamber from materials that are impermeable to the substances. Additionally or alternatively, a barrier layer or coating could be formed from such impermeable materials to prevent the substances from entering the lens chamber 201 or some other element or structure of the electrowetting lens 200. For example, a barrier could be formed (e.g., on an internal surface of the first 210*a* and/or second 210*b* elements) from a chloride-impermeable material to prevent chloride ions present in the aqueous humor from entering the lens chamber 201 or from entering some other material or volume of the lens 200. Such a material could include a polymeric material, a metal foil or deposited metal layer, or some other material(s). Such materials could be substantially transparent to visible light.

In some examples, components of the electrowetting lens 200 could be composed of a self-healing material. For example, the first 210*a* and/or second 210*b* elements could be at least partially formed from self-healing materials. Such self-healing materials could be provided to maintain the integrity of the lens chamber 201 or of other volumes of the electrowetting lens 200 against bulk fluid flows into or out of such volumes (e.g., between the lens chamber 201 and the aqueous humor of an eye). In some examples, such self-healing materials may be degraded and/or their ability to self-heal diminished by exposure to chloride ions or other substances present in the aqueous humor and/or in the fluids 230*a*, 230*b* of the electrowetting lens 200. In such examples, an impermeable material (e.g., a chloride-impermeable material) could be used to form a barrier between the chloride ions or other substances present in the aqueous humor and the self-healing material.

III. Example Freezing and/or Melting of a Fluid in an Electrowetting Lens

It can be beneficial for one or more substances of an electrowetting lens to be solid during implantation of the electrowetting lens into an eye. Such substance(s) being solid can prevent mixing of the substances and/or wetting of internal surfaces by the solidified substances during folding, rolling, unfolding, unrolling, or other manipulations of the electrowetting lens (e.g., of a flexible electrowetting lens) during implantation or during other processes (e.g., during fabrication of the electrowetting lens). By preventing mixing of the substances and/or preventing wetting of internal surfaces by one or more of the substances, optical properties (e.g., clarity, symmetry of refraction about an axis, wavelength-dependent refraction or absorption) or other properties (e.g., of the relationship between an applied voltage and the optical power of the lens) of the electrowetting lens may be preserved and/or improved.

The melting point of such substances within the electrowetting lens can be less than body temperature (e.g., 37 degrees Celsius) such that the substances are fluid when the electrowetting lens is located within a body (e.g., within an eye of a body). To prevent solidification of such substances in response to reduction in the temperature of a body, or due to a particular body's average temperature being less than 37 degrees Celsius, the melting points of such substances could be less than a temperature that is less than the average body temperature by some nonzero amount. For example, the melting point of one or more substances within an electrowetting lens could be less than 36 degrees Celsius, or less than 35 degrees Celsius. The melting point of such a substance could be less than body temperature by a small amount to minimize an amount of cooling required to maintain the electrowetting lens below the melting point while exposed to a body, in order to maximize an amount of time between exposure of the electrowetting lens to a body (e.g., by insertion through a corneal incision) and melting of the substance(s), or to provide some other benefit.

The melting point of such substances within the electrowetting lens can be greater than some specified temperature in order to facilitate maintenance of the substance in a frozen or otherwise solidified state prior to implantation. For example, the melting point of one or more substances within an electrowetting lens could be greater than 0 degrees Celsius. In some examples, the melting point of one or more of the substances could be greater than room temperature, such that the substance could be maintained in a frozen or otherwise solidified state by being exposed to (e.g., by being stored in) an environment at room temperature. For example, the melting point of such a substance could be greater than 15 degrees Celsius, or greater than 30 degrees Celsius. Additionally or alternatively, one or more substances within an electrowetting lens could be kept in a frozen or otherwise solidified state by being actively cooled or otherwise exposed to a fluid or object below the melting temperature of the one or more substances.

The melting point of one or more substances in an electrowetting lens (e.g., of a substance that, when melted, forms a nonpolar fluid of the lens) could be specified by controlling one or more properties of the substances. For example, a substance could be made from a combination of a fluid having a melting point greater than the desired melting point and one or more solutes could be added to the fluid to reduce the melting point of the combination to correspond to the desired melting point. For example, a salt or alcohol (e.g., butanediol) could be added to an aqueous fluid, or a phenylated silicone oil (e.g., polyphenylmethylsiloxane) could be added to a nonpolar fluid (e.g., a silicone oil like polydimethylsiloxane). Additionally or alternatively, a ratio of two or more fluids comprising the substance could be set such that the melting point of the combination corresponds to the desired melting point. In some examples, two (or more) different linear alkanes could be combined. In an example, a first linear alkane having a melting point greater than the desired melting point (e.g., nonadecane) and a second linear alkane having a melting point lower than the desired melting point (e.g., hexadecane) could be combined in a ratio related to the desired melting point. Yet further, a mean chain length, degree or type of branching or cross-linking, a polydispersity, or some other property of a substance could be controlled such that the substance has a desired melting point.

Figure 3A:
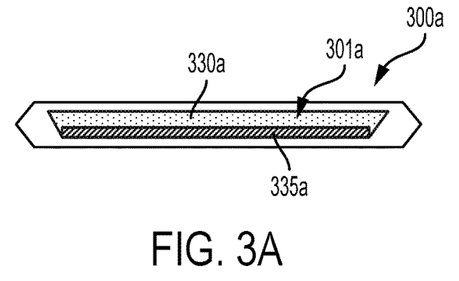
FIG. 3A is a side cross-section view of an example eye-implantable device.

FIG. 3A shows an example electrowetting lens 300*a* (e.g., of an eye-implantable device) that includes a first substance 335*a* (e.g., a saline solution that is isotonic with respect to aqueous humor in an eye) and a second substance 330a (e.g., a silicone oil or some other nonpolar substance) disposed within a lens chamber 301a of the electrowetting lens 300a. The electrowetting lens is being maintained at a temperature (e.g., at a room temperature between 15 degrees Celsius and 30 degrees Celsius) that is less than a melting point of the second substance 330a such that the second substance 330a is frozen or otherwise solidified.

The electrowetting lens 300a could be fabricated in a variety of ways. In some examples, the lens chamber 301a could be partially formed (e.g., by injection molding or otherwise forming a polymeric material that at least partially forms the lens chamber 310a) and the first 330a and second 335a substances deposited, as fluids or otherwise, within the lens chamber 301a. The lens chamber 301a could then be completed, e.g., by disposing and/or forming a lid atop the portions of the chamber already formed.

In some examples, this could include filling the partially-formed lens chamber with a first substance 330a comprising saline (or some other aqueous solution) and displacing any bubbles formed on the walls of the lens chamber (e.g., by ultrasonic cleaning, by rinsing, by adding the saline in a reduced-pressure environment, and/or by degassing the saline prior to applying it to the lens chamber). The second substance 335a, which may comprise a silicone oil, a mixture of linear alkanes, or some other nonpolar substance(s), may then be disposed on a specified surface of the electrowetting lens 300a beneath the first substance 330a. This could include heating the second substance 335a and/or applying the second substance 335a in a heated environment so that the second substance 335a is fluid in the lens chamber 301a. Additionally or alternatively, the second substance 335a could be applied, as a fluid, to the partially-formed lens chamber 301a first, then frozen or otherwise solidified (e.g., by application of cooling to the electrowetting lens 300a). The first substance 330a could then be applied atop the second substance 335a. Bubbles could be displaced from within the lens chamber 301a and/or prevented from forming by a number of methods, including but not limited to applying ultrasonic energy to the electrowetting lens 300a during fabrication, by rinsing the lens chamber 301a with an excess of one or both of the first 330a and second 335b substances, by adding one or both of the substances 330a, 335a as fluids in a reduced-pressure environment, and/or by degassing one or both of the substances 330a, 335a prior to applying them to the lens chamber 301a.

The overall shape (e.g., thickness, thickness profile) of the frozen or otherwise solidified substance(s) of an electrowetting lens as described herein (e.g., 300a) could be controlled in order to facilitate implantation of the electrowetting lens. For example, the amount or thickness of a substance within the electrowetting lens could be reduced in areas where it is more likely that the substance will contact an opposing internal surface of the electrowetting lens during manipulation and/or implantation of the lens (e.g., at locations near the center of the electrowetting lens.

Figure 3B:
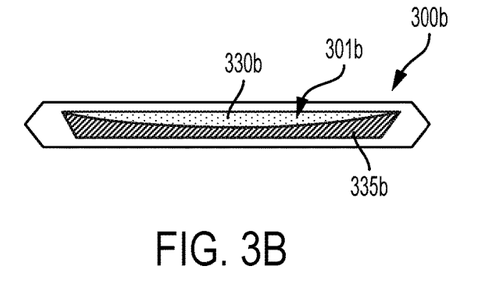
FIG. 3B is a side cross-section view of an example eye-implantable device.

Such a specified distribution of the substance could be accomplished in a variety of ways. In some examples, the substance could be disposed in fluid form by a needle, by screen printing, or by some other method. Additionally or alternatively, the shape of such an applied substance could be controlled by heating the electrowetting lens to melt all of the substance (e.g., by heating the lens to body temperature) and applying voltages to electrodes the electrowetting lens). This is illustrated by way of example in FIG. 3B. FIG. 3B shows another electrowetting lens 300b (which may be the same electrowetting lens as shown in FIG. 3A) that includes first 330b and second 335b substances disposed within a lens chamber 301b. As shown in FIG. 3B, the second substance 335b is frozen or otherwise solidified and is thinner at the middle of the lens 300a than at the edges. Such a distribution of the second substance 335b within the lens chamber 301b could be accomplished by applying sufficient heat to melt the second substance 335b and then applying voltages to electrodes disposed on internal surfaces of the electrowetting lens 300b. Such electrodes could include electrodes used to control the optical power of the electrowetting lens 300b and/or could include further electrodes used to control the shape or distribution of the second substance 335b within the lens chamber 301b during fabrication and/or implantation of the electrowetting lens 300b.

Figure 3C:
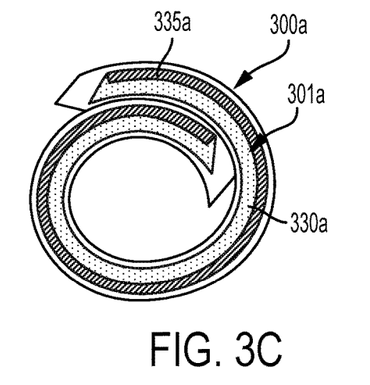
FIG. 3C is a side cross-section view of the example eye-implantable device of FIG. 3A after being rolled up.
Figure 3D:
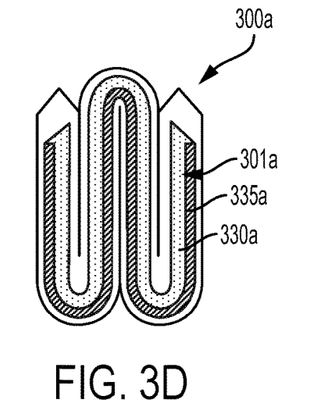
FIG. 3D is a side cross-section view of the example eye-implantable device of FIG. 3A after being folded up.

Once the electrowetting lens has been fabricated, and the substance(s) within the lens have been frozen or otherwise solidified (e.g., by application of cooling, by being maintained at a specified temperature below a melting point of the substance(s)), the electrowetting lens may be folded, rolled, bent, or otherwise manipulated. Such manipulation could permit the electrowetting lens to be inserted via an incision that is smaller than a diameter or other characteristic dimension of the electrowetting lens. For example, the electrowetting lens could be rolled, folded, or otherwise manipulated such that it can be inserted through an incision that is less than 4 millimeters wide, or less than 2 millimeters wide. FIG. 3C shows the electrowetting lens 300a rolled up, with the second substance 335a frozen or otherwise solidified. Note that an electrowetting lens could be rolled more or fewer times, or could be rolled more tightly or more loosely, or could differ in some other respect from that shown in FIG. 3C. FIG. 3D shows the electrowetting lens 300a folded into thirds, with the second substance 335a frozen or otherwise solidified. Note that an electrowetting lens could be folded more or fewer times, could be folded into uneven segments, or could differ in some other respect from that shown in FIG. 3D.

Figure 3E:
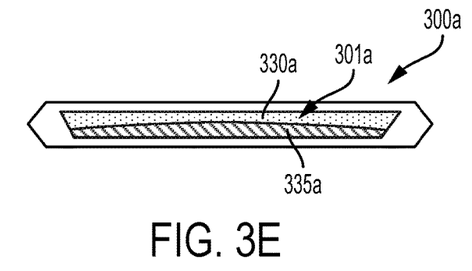
FIG. 3E is a side cross-section view of the example eye-implantable device of FIG. 3D after being unfolded.

Once inserted into an eye (e.g., via an incision), the electrowetting lens may be positioned, flattened, or otherwise manipulated to facilitate operation of the electrowetting lens to provide an electronically-controllable optical power to an eye. In response to exposure to heat from the eye, the substances within the electrowetting lens could become fluid to permit such operation of the electrowetting lens. This is shown in FIG. 3E, which shows the electrowetting lens 300a flattened, with both the first substance 330a and second substance 335a fluid in response to exposure to the heat, at body temperature, of an eye into which the lens 300a has been implanted. In order to prevent premature melting of such substances, the temperature of the electrowetting lens could be maintained below the melting point of substance(s) within the lens until after insertion of the lens into the eye, until after positioning the lens at a specified location within the eye, after unfolding or unrolling the lens, or after some other processes have occurred. This could include, immediately prior to inserting the electrowetting lens into an eye, maintaining the electrowetting lens at a temperature that is well below the melting point(s) of the substance(s) within the electrowetting lens. Additionally or alternatively, cooling could be applied to the electrowetting lens while inserting the lens into the eye, while placing the lens at a specified location within the eye, or while performing some other procedure.

Such cooling could be accomplished by applying cooling to the lens via forceps or other instruments that are configured to apply such cooling, e.g., by including a thermoelectric cooler, channels for the flow of cooling fluid, or some other cooling means. For example, a needle used to insert the lens, folded or rolled up, through the incision could include fluid channels or other means for applying cooling to the eye-implantable device. Additionally or alternatively, such cooling could be accomplished by applying cooling to the eye itself. For example, cooling could be applied to the outside of the eye using a thermoelectric cooler, a bath of chilled saline, or other means in contact with the external surface of the eye. Additionally or alternatively, the eye could be cooled by irrigating the anterior chamber or other regions of the eye with chilled saline.

IV. Example Electronics of Devices

Figure 4:
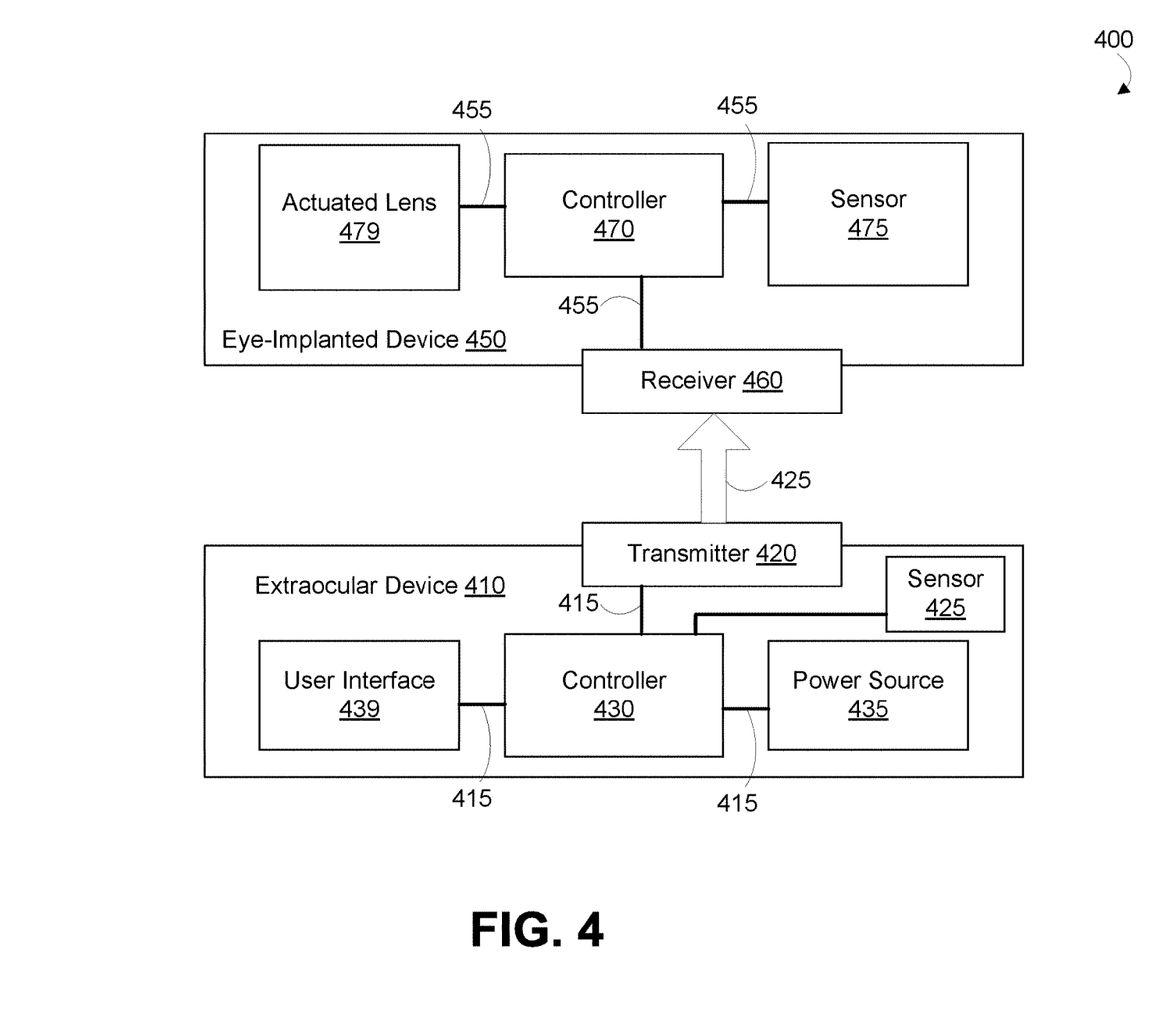
FIG. 4 is a block diagram of an example system that includes an extraocular device that can provide power to an eye-implanted device.

FIG. 4 is a block diagram of a system 400 that includes an extraocular device 410 wirelessly transmitting wireless signals 425 to an eye-implanted device 450. The wireless signals 425 may include wireless power signals to provide power to the eye-implanted device 450, control signals to control the operation of the eye-implanted device 450 (e.g., to control an optical power provided by an adjustable lens 479 of the eye-implanted device 450), or other wireless signals. The extraocular device 410 may be a body-mounted device, e.g., a contact lens, a head-mounted display, or some other type of head-mounted device. Additionally or alternatively, the extraocular device 410 may be a handheld device like a cell phone, a device incorporated into furniture, e.g., into a bed to facilitate charging of the eye-implantable device 450 while a user sleeps, or may take some other form(s). The eye-implanted device 450 is implanted on or within an eye of a user.

The extraocular device 410 includes a controller 430, user interface 439, a transmitter 420, a power source 435, and a sensor 425. The transmitter 420 can be operated to wirelessly transmit power, commands, or other signals to the eye-implanted device 450 in an eye. The transmitter 420, the controller 430, the power source 435, the user interface 439, and the sensor 425 can all be connected together via interconnects 415, e.g., via wires, cables and/or, patterns of metallic traces formed on a printed circuit board or other substrate material on which the components may be disposed. Further, the transmitter 420 could comprise metallic traces or patterns formed on such a substrate material (e.g., to form antennas, impedance matching elements, plates of capacitors, electrodes, mirrors or diffraction gratings).

The transmitter 420 can include light-emitting elements (e.g., LEDs, lasers, VCSELs), radio-frequency electromagnetic energy-transmitting elements (e.g., antennas, coils), elements configured to inject a time-varying current into tissues or fluids of a body (e.g., electrodes), or other elements configured to transmit, e.g., power from the power source 435 to the implanted device 450. The transmitter 420 could be configured to control an intensity, a phase, a frequency, a polarization, a direction, or some other properties of wireless signals transmitted from the transmitter 420 to indicate information. The transmitter 420 could be configured to provide power to the eye-implanted device 450 when the extraocular device 410 is not mounted to an eye or body of a user (e.g., when the user is sleeping in a bed such that the eye-implanted device 450 within an eye of the user is proximate to the extraocular device 410) or while the extraocular device 410 is mounted to the eye or body of the user.

The power source 435 may provide power to the extraocular device 410 to, e.g., to recharge a rechargeable battery of the power source 435 in embodiments wherein the extraocular device 410 is an eye-mountable device. The power source 435 could include a battery (e.g., single-use alkaline batteries, rechargeable lithium-polymer batteries), a solar cell, connection to a mains power source, or some other source of energy.

The sensor 425 may be configured to detect physiological properties (e.g., a pupillary diameter of an eye), environmental parameters (e.g., an ambient light level, a distance between eyes of a user and an object at which the user is looking), to detect movements of the eye and/or eyelids of a user (e.g., to detect a vergence of the eyes), or to otherwise detect physical parameters that may be relevant to the operation of the extraocular device 410 and/or the eye-implanted device 450. The user interface 439 may include displays, inputs, speakers, microphones, touchscreens, buttons, scroll wheels, or other elements to facilitate receiving information (e.g., commands) from a user and/or to provide information (e.g., a command interface, a battery status or other information about the devices 410, 450) to a user. For example, the user interface 439 may be operated to receive commands from a user related to a desired optical power of the eye-implanted device 450 and/or information about a distance a user wishes to see or some other information related to an optical power that could be desired from the eye-implanted device 450.

The eye-implanted device 450 includes a controller 470, a sensor 475, a receiver 460, and an adjustable lens 479. The adjustable lens 479 could be an electrowetting lens as described herein. The receiver 460 can be operated to receive power or other wireless signals 425 wirelessly transmitted by the transmitter 420 (e.g., from the power source 435 of the extraocular device 410). This could include receiving optical signals (e.g., via a photovoltaic cell, photodiode, or other light-sensitive elements), radio frequency electromagnetic signals (e.g., via an antenna, via a coil), an electrical current or potential in the tissues or fluids surrounding the eye-implanted device 450 (e.g., via electrodes), or receiving some other signals wirelessly transmitted from the extraocular device 410. The eye-implanted device 450 could include a capacitor, a battery, or other type of energy storage device to provide energy for use by the device 450 when power is unavailable from the other systems (e.g., when the extraocular device 410 is not mounted to or otherwise proximate to the eye-implanted device 450).

The sensor 475 is configured to detect a physiological property of the body (e.g., a pressure or force, a biopotential, a light intensity). In a particular example, the sensor 475 could be an accommodation sensor configured to detect, directly or indirectly, accommodation forces exerted on a lens capsule of the eye, e.g., by detecting a force or pressure within the lens capsule via haptics, via an elastic material disposed in the lens capsule, via detection of electrical activity of the ciliary muscles, or via some other means.

The adjustable lens 479 is operable to control an optical power that is provided to the eye by the adjustable lens 479. Operating the adjustable lens 479 to control the optical power of the lens could include applying a voltage to a liquid crystal of the lens 479, applying a voltage to electrodes of an electrowetting adjustable lens 479 or operating a pump or some other element to control a pressure and/or disposition of a fluid within the lens 479, or controlling the optical power of the lens by some other method.

The eye-implanted device 450 and/or extraocular device 410 could include additional or alternative elements, and could include more or fewer elements than those illustrated in FIG. 4. This could include the eye-implanted device 450 including elements configured to transmit wireless signals to the extraocular device 410 and the extraocular device 410 including elements configure to receive such transmitted signals. In such an example, the eye-implanted device 450 and the extraocular device 410 could additionally include a transmitter and receiver, respectively. Additionally or alternatively, the illustrated receiver 460 and transmitter 420 could be configured as transceivers to facilitate bidirectional communication and/or to share one or more elements (e.g., antennas, filters, coils, power conditioning systems) in common with other elements configured to facilitate bidirectional communication.

It is noted that the block diagram shown in FIG. 4 is described in connection with functional modules for convenience in description. However, embodiments of the extraocular device 410 and/or eye-implanted device 450 can be arranged with one or more of the functional modules ("sub-systems") implemented in a single chip, integrated circuit, and/or physical feature. That is, the functional blocks in FIG. 4 need not be implemented as separated modules. Moreover, one or more of the functional modules described in FIG. 4 can be implemented by separately packaged chips or other components electrically connected to one another. Further, note that an extraocular device and/or an eye-implantable device as described herein could include additional or alternative components to those shown in FIG. 4 (e.g., additional sensors, adjustable lenses, displays, retinal stimulator arrays, electrodes, batteries, controllers, transmitters, receivers, stimulators, etc.). For example, the power source 435 of the extraocular device 410 could be a single-use battery and the extraocular device 410 could be operated as a single-use device (e.g., operated until the battery of the power source 435 is depleted and then discarded and/or recycled).

V. Example Methods

Figure 5:
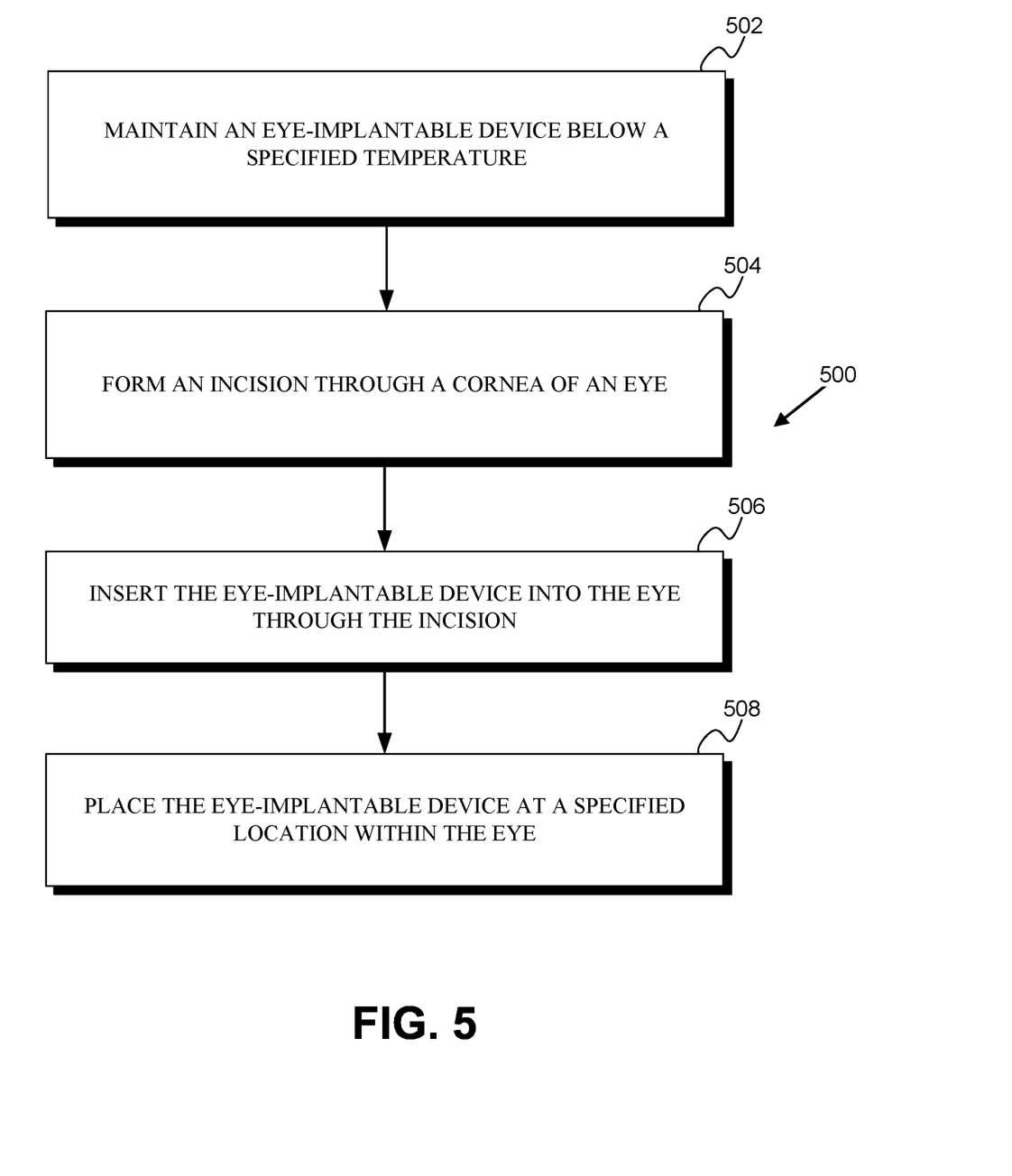
FIG. 5 is a flowchart of an example process.

FIG. 5 is a flowchart of a method 500 for implanting an eye-implantable device within a human eye. The device includes an electrowetting lens as described herein that includes (i) a lens chamber, (ii) a first substance that is disposed within the lens chamber and that has a first melting point that is less than 37 degrees Celsius, (iii) a second substance that is disposed within the lens chamber, that has a second melting point that is between 0 degrees Celsius and 37 degrees Celsius, that is immiscible with the first substance when the first substance and the second substance are both fluid, and that differs from the second substance with respect to refractive index when the first substance and the second substance are both fluid, (iv) a first electrode that is disposed on an internal surface of the lens chamber in contact with the first substance, and (v) a second electrode that includes a dielectric coating and that is disposed on an internal surface of the lens chamber in contact with at least one of the first substance or the second substance.

The method 500 includes maintaining the eye-implantable device below a specified temperature (502). The specified temperature is less than or equal to at least one of the first melting point or the second melting point, such that maintaining the eye-implantable device below the specified temperature results in the first and/or second substances freezing and/or remaining in a frozen or otherwise solid state. Maintaining the eye-implantable device below the specified temperature could include applying cooling to the eye-implantable device, e.g., using a thermoelectric cooler, a refrigerated fluid or other substance, a compressor and evaporator, a thermally conductive element, a heat pipe, or some other means for cooling an object. Additionally or alternatively, maintaining the eye-implantable device below the specified temperature could include exposing the eye-implantable device to an environment that has a temperature at or below the specified temperature. For example, the melting point of one or both of the first or second substances could be above room temperature (e.g., above 15 degrees Celsius, above 30 degrees Celsius) and the device could be maintained below the specified temperature by storing the device in a room having a temperature at or below room temperature. Maintaining the eye-implantable device below the specified temperature could include applying cooling to the eye-implantable device to decrease the temperature of eye-implantable device.

The method 500 includes forming an incision through the cornea of the eye (502). This could include operating a scalpel, a laser, a diamond blade, a metal blade, or some other instruments to create an incision through the cornea. The incision could be created by creating multiple separate cuts or incisions into the cornea. For example, a first cut could be made perpendicular to the surface of the sclera, and one or more subsequent cuts could be made at other angles (e.g., tangential angles) relative to the sclera. The incision could be formed to be water-tight, to cause a minimum of astigmatism, or to satisfy some other considerations. The formation of the incision could be accompanied by mechanical stabilization of the eye (e.g., using fixation rings, forceps, or other means), administration of topical or global anesthesia, or some other steps. The formed incision could have a length or other dimension within some specified range; e.g., the incision could be less than 4 millimeters long, or less than 2 millimeters long.

The method 500 includes inserting the eye-implantable device into the eye through the incision (504). This could include using forceps or some other means to insert the eye-implantable device through the incision. Additionally or alternatively, the eye-implantable device could include tabs, rods, or other features to facilitate such insertion. Such features could be later removed from the eye-implantable device (e.g., by cutting, crimping, laser cutting, or some other means) or could remain as part of the eye-implantable device following implantation.

The method 500 further includes placing the eye-implantable device at a specified location within the eye (506). As noted above for insertion of the eye-implantable device through the incision, this could include instruments to manipulate and position the eye-implantable device and/or using tabs, rods, or other features of the eye-implantable device. Placing the eye-implantable device at the specified location could include inserting the device through additional incisions or other surgically formed features of the eye (e.g., an incision through the iris, through a hole formed in the lens capsule of the eye) and/or through natural features of the eye (e.g., through the pupil of the iris). The specified location could be within the lens capsule, in the anterior capsule, in the posterior capsule, in the vitreous humor, or in some other location of the eye. Placing the eye-implantable device at the specified location could include manipulating haptics or other features of the device and/or additional implanted elements in order to secure the device at the specified location, to facilitate interactions between the device and the eye (e.g., to facilitate detection of accommodation forces applied to the lens capsule of the eye), or to provide some other benefit. Placing the eye-implantable device at the specified location could include assembling multiple different elements of the device together, e.g., assembling an electrowetting lens together with an electronics module to form the eye-implantable device.

Maintaining the eye-implantable device below the specified temperature (502) could include maintaining the eye-implantable device below the specified temperature while inserting the eye-implantable device into the eye through the incision, while placing the eye-implantable device at the specified location within the eye, or while performing some other procedure. This could be accomplished by applying cooling to the eye-implantable device via forceps or other instruments that are configured to apply such cooling, e.g., by including a thermoelectric cooler, channels for the flow of cooling fluid, or some other cooling means. For example, a needle used to insert the eye-implantable device, folded or rolled up, through the incision could include fluid channels or other means for applying cooling to the eye-implantable device. Additionally or alternatively, this could be accomplished by applying cooling to the eye itself. For example, cooling could be applied to the outside of the eye using a thermoelectric cooler, a bath of chilled saline, or other means in contact with the external surface of the eye. Additionally or alternatively, the eye could be cooled by irrigating the anterior chamber or other regions of the eye with chilled saline.

The method 500 could include additional steps or elements in addition to those depicted in FIG. 5 (i.e., 502, 504, 506, 508). For example, the method 500 could include adding or removing material, e.g., adding or removing an amount of the first or second fluids, from the eye-implantable device. This could be performed using a needle (e.g., by piercing a septum of the device with the needle), using tubes connected between the device and external systems, or via some other method. In examples wherein tubes are used, the method 500 could further include severing such tubes (e.g., via mechanical and/or ultrasonic crimping and cutting, via mechanical cutting, via laser cutting, via application of a shearing or tension force to the tubes) and removing portions of the severed tubes from the eye. The method 500 could include further surgical manipulations of the eye, e.g., the formation of a hole in the lens capsule and/or the removal of the crystalline lens, the removal of a previously implanted device (e.g., a static IOL). The method 500 could include programming and/or testing the eye-implantable device. In some examples, the eye-implantable device could be rolled, folded, or otherwise manipulated to reduce one or more dimensions of the device (e.g., in order to facilitate insertion of the device through a smaller incision) and the method 500 could include unrolling, unfolding, or otherwise manipulating the eye-implantable device subsequent to inserting the device through the incision. In some examples, the eye-implantable device could be implanted through the sclera or via some other route, and the method 500 could include forming alternative incisions (e.g., through the sclera) and inserting the device through such alternative incisions.

VI. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. An eye-implantable device comprising:
   an electrowetting lens, wherein the electrowetting lens comprises:
     a lens chamber;
     a polymeric material, wherein the polymeric material at least partially encloses the lens chamber;
     a first substance disposed in the lens chamber, wherein the first substance has a first melting point that is less than 37 degrees Celsius;
     a second substance disposed in the lens chamber, wherein the second substance has a second melting point that is between 0 degrees Celsius and 37 degrees Celsius, wherein the second substance is immiscible with the first substance when the first substance and the second substance are both fluid, and wherein a refractive index of the second substance differs from a refractive index of the first substance when the first substance and the second substance are both fluid;
     a first electrode, wherein the first electrode is disposed on an internal surface of the polymeric material in contact with the first substance; and
     a second electrode, wherein the second electrode is disposed on an internal surface of the polymeric material in contact with at least one of the first substance or the second substance, wherein the second electrode comprises a dielectric coating.

2. The eye-implantable device of claim 1, wherein the second melting point is greater than 15 degrees Celsius.

3. The eye-implantable device of claim 2, wherein second melting point is greater than 30 degrees Celsius.

4. The eye-implantable device of claim 1, wherein the polymeric material is flexible such that the electrowetting lens can be folded.

5. The eye-implantable device of claim 1, wherein the polymeric material comprises 2-phenylethyl acrylate units and 2-phenylethyl methacrylate units.

6. The eye-implantable device of claim 1, wherein the second substance comprises a silicone oil.

7. The eye-implantable device of claim 6, wherein the silicone oil comprises polydimethylsiloxane.

8. The eye-implantable device of claim 1, wherein the second substance comprises a first linear alkane and a second linear alkane and wherein the second melting point is related to a ratio between an amount of the first linear alkane in the second substance and an amount of the second linear alkane in the second substance.

9. The eye-implantable device of claim 8, wherein the first linear alkane comprises hexadecane and wherein the second linear alkane comprises nonadecane.

10. The eye-implantable device of claim 1, wherein the lens chamber is permeable to water in an aqueous humor of a human eye and wherein the first substance comprises a conductive fluid having osmolality between 298 milliosmoles per kilogram and 310 milliosmoles per kilogram.

11. The eye-implantable device of claim 1, wherein the first substance comprises a conductive fluid that comprises butanediol.

12. The eye-implantable device of claim 1, wherein the refractive index of the second substance differs from the refractive index of the first substance by more than 0.1 when the first substance and the second substance are both fluid.

* * * * *